(12) United States Patent  (10) Patent No.: US 7,854,511 B2
Molnar et al.  (45) Date of Patent: Dec. 21, 2010

(54) APPARATUS, METHODS AND SYSTEMS FOR NON-INVASIVE OCULAR ASSESSMENT OF NEUROLOGICAL FUNCTION

(75) Inventors: Lance Molnar, Morgantown, WV (US); John V. Linberg, Morgantown, WV (US); James Vernon Odom, Morgantown, WV (US)

(73) Assignee: Eye Marker Systems, Inc., Morgantown, WV (US)

( * ) Notice: Subject to any disclaimer, the term of this patent is extended or adjusted under 35 U.S.C. 154(b) by 0 days.

(21) Appl. No.: 12/244,358

(22) Filed: Oct. 2, 2008

(65) Prior Publication Data

US 2009/0147217 A1 Jun. 11, 2009

Related U.S. Application Data

(60) Provisional application No. 60/960,553, filed on Oct. 3, 2007.

(51) Int. Cl.
A61B 3/10 (2006.01)
(52) U.S. Cl. .................. 351/221; 351/218; 351/246
(58) Field of Classification Search ................ 351/221, 351/246, 218, 210, 206, 205, 200; 359/375, 359/362, 404
See application file for complete search history.

(56) References Cited

U.S. PATENT DOCUMENTS

| 4,850,691 | A  | 7/1989  | Gardner et al. |
| 4,993,825 | A  | 2/1991  | Abe et al. |
| 5,125,730 | A  | 6/1992  | Taylor et al. |
| 5,583,795 | A  | 12/1996 | Smyth |
| 5,778,893 | A  | 7/1998  | Potter |
| 6,022,109 | A  | 2/2000  | Dal Santo |
| 6,162,186 | A  | 12/2000 | Scinto et al. |
| 6,260,968 | B1 | 7/2001  | Stark et al. |
| 6,305,804 | B1 | 10/2001 | Rice et al. |
| 6,382,792 | B1 | 5/2002  | Khoury et al. |
| 6,387,618 | B1 | 5/2002  | Kolanko et al. |
| 6,477,394 | B2 | 11/2002 | Rice et al. |
| 6,544,193 | B2 | 4/2003  | Abreu |
| 6,547,394 | B2 | 4/2003  | Doherty |
| 6,565,210 | B2 | 5/2003  | Kobayashi et al. |
| 6,626,537 | B1 | 9/2003  | Odom et al. |

(Continued)

FOREIGN PATENT DOCUMENTS

WO WO-2004/056278 A2 7/2004

(Continued)

OTHER PUBLICATIONS

International Search Report and Written Opinion for PCT/US08/78573, dated Dec. 2, 2008.

(Continued)

*Primary Examiner*—Hung X Dang
(74) *Attorney, Agent, or Firm*—Patton Boggs LLP

(57) ABSTRACT

A portable, non-invasive binocular scanning apparatus for rapid assessment of neurological function in cases of potential trauma, disease, and/or exposure to chemical treat agents. The scanning apparatus may utilize a combination of light sources for the measurement and assessment of pupillary response, retinal imagery, and/or other ophthalmologic biomarkers. The scanning apparatus can detect and assess a wide range of neurological and physiological conditions by obtaining pertinent measurements from the retina and pupil in real time.

28 Claims, 5 Drawing Sheets

U.S. PATENT DOCUMENTS

| | | | |
|---|---|---|---|
| 6,631,989 | B2 | 10/2003 | Odom et al. |
| 6,637,885 | B2 | 10/2003 | Petrali |
| 7,204,590 | B1 | 4/2007 | Lenoir |
| 7,703,918 | B2 | 4/2010 | Kolanko et al. |
| 2001/0055095 | A1 | 12/2001 | D'Souza et al. |
| 2002/0024633 | A1* | 2/2002 | Kim et al. .................. 351/206 |
| 2002/0047989 | A1 | 4/2002 | Shibata |
| 2002/0171805 | A1 | 11/2002 | Odom et al. |
| 2004/0207811 | A1 | 10/2004 | Elsner |
| 2005/0057721 | A1 | 3/2005 | Kolanko et al. |
| 2006/0146284 | A1 | 7/2006 | Collins et al. |
| 2008/0212026 | A1 | 9/2008 | Molnar et al. |

FOREIGN PATENT DOCUMENTS

| | | |
|---|---|---|
| WO | WO-2008/030944 A2 | 3/2008 |
| WO | WO-2009/046189 A1 | 4/2009 |

OTHER PUBLICATIONS

International Search Report for PCT/US03/41220 dated Oct. 5, 2004.
International Search Report and Written Opinion for PCT/US07/077739, dated Aug. 20, 2008.
U.S. Appl. No. 12/718,342, published Mar. 5, 2010, Kolanko et al.
In the U.S. Patent and Trademark Office, Office Action in re: U.S. Appl. No. 11/896,801, dated Sep. 2, 2009, 12 pages.
In the U.S. Patent and Trademark Office, Restriction Requirement in re: U.S. Appl. No. 10/740,979, dated Mar. 2, 2007, 5 pages.
In the U.S. Patent and Trademark Office, Office Action in re: U.S. Appl. No. 10/710,979, dated May 24, 2007, 10 pages.
In the U.S. Patent and Trademark Office, Final Office Action in re: U.S. Appl. No. 11/740,979, dated Feb. 3, 2009, 10 pages.
In the U.S. Patent and Trademark Office, Office Action in re: U.S. Appl. No. 10/740,979, dated May 20, 2009, 7 pages.
In the U.S. Patent and Trademark Office, Notice of Allowance in re: U.S. Appl. No. 10/740,979, dated Oct. 16, 2009, 9 pages.
European Supplemental Search Report EP 07814707, dated Jan. 28, 2010.
Molnar et al., "Ocular Scanning Instrumentation: Rapid Diagnosis of Chemical Threat Agent Exposure," *Proceedings of SPIE -The International Society for Optical Engineering - Sensors, and Command, control, Communications, and Intelligence (C3I) Technologies for Homeland Security and Homeland Defense III 2004 SPIE US*, vol. 5403, No. Part 1, 2004, pp. 60-67, XP002565637.

* cited by examiner

APPARATUS, METHODS AND SYSTEMS FOR NON-INVASIVE OCULAR ASSESSMENT OF NEUROLOGICAL FUNCTION

CROSS-REFERENCE TO RELATED APPLICATION

This application claims priority to U.S. Provisional Patent Application No. 60/960,553, filed Oct. 3, 2007, the contents of which are incorporated by reference herein in its entirety.

FIELD OF THE INVENTION

The present invention relates generally to the field of ophthalmology, and more particularly to apparatus, methods and systems for portable, rapid assessment of neurological and physiological function by assessing ophthalmologic biomarkers.

BACKGROUND OF THE INVENTION

Ophthalmologic biomarkers are measurable ocular features or facets that can be used to detect and assess various pathological and non-pathological conditions affecting a subject. Non-limiting examples of ophthalmologic biomarkers may include pupillary responsiveness (pupil size, pupillary light reflex, pupil motility/kinetics), retinal imagery (retinal blood vessel coloration, retinal blood vessel dimensions, retinal blood vessel architecture, ischemic spots), optical nerve characteristics, exudate appearance, and cellular degeneration. A subject's ophthalmologic biomarkers may reveal a variety of neurological and physiological conditions caused by disease, trauma, and/or exposure to chemical threat agents, see, e.g., U.S. Pat. No. 6,631,989 to Odom et al. Non-limiting examples of trauma and disease may include internal and external traumas, inadequate nutritional status, altered cognitive states, and various congenital, vascular, autoimmune, and connective tissue disorders.

Due to the usefulness of ophthalmologic biomarkers in identifying conditions of interest, various devices and techniques exist for monitoring pupil size and responsiveness characteristics. These systems are generally referred to as pupilometry systems or pupilometers. A variety of pupillary defects are useful in detecting and assessing bilateral afferent or efferent pupillary defects, traumatic injuries to the optic nerve and/or the central nervous system, diseases which affect the central nervous system, and/or conditions caused by exposure to chemical threat agents.

Pupillary size and responsiveness have long been a critical component in clinical assessment of subjects with neurological and physiological conditions. For example, Relative Afferent Pupillary Defect (RAPD), also termed the Marcus-Gunn pupil, is a quantifiable clinical finding that may result from a variety of physiological conditions that affect the retina or optic nerve. In general, RAPD occurs concomitantly with significant optic nerve or retinal disease and/or abnormal condition due to an asymmetrical effect on the two eyes. Diseases or conditions that affect the two eyes symmetrically generally will not be evidenced by RAPD testing. Prominent conditions which may lead to RAPD may include:

Amblyopia with visual acuity of 20/400 or worse;
Cerebral vascular disease;
Optic nerve disorders such as glaucoma, ischemic optic neuropathies, optic atrophy after papilledema, optic neuritis, optic nerve infections/inflammations, optic nerve tumor, orbital disease, and optic nerve damage via radiation, surgery, and other direct insults; or
Retinal causes, such as intraocular tumor, ischemic ocular or retinal disease, retinal detachment, retinal infection, or severe macular degeneration.

The swinging-flashlight test is widely known and used for evaluating neuro-ophthalmologic defects, and more particularly, RAPD. Briefly, this test is performed in a dimly lit room using a relatively strong, directional light source. Pupillary reactions are observed as the light shines in one eye and then the other in rapid succession. Typically, this swinging back-and-forth between eyes with the light is repeated multiple times until the examiner is confident with respect to the reactivity of the iris/pupil in each eye to both direct and consensual light application. Direct light application means observing the pupillary response in the same eye to which light stimulus is being applied. Consensual light application means observing the pupillary response in the eye opposite to that which is receiving light stimulus.

Normally, when either eye is exposed to direct light, both will constrict. As light shifts from one eye to the other, both pupils begin to dilate, only to re-constrict as the light reaches the opposite eye. In an individual with an afferent lesion, such as in RAPD, shining light into an unaffected eye will cause both pupils to constrict (as normal), whereas shining light into the affected eye will yield a diminished or absent constrictive response in both eyes. Four gradations of this effect can be delineated, and include:

No RAPD (both pupils constrict equally without evidence of pupillary re-dialiation);
Mild RAPD (one pupil shows a weak initial constriction, followed by dilation to a greater size);
Moderate RAPD (one pupil shows sustained constriction, followed by dilation to a greater size); and
Severe RAPD (one pupil shows an immediate dilation to a greater size).

A byproduct of the swinging-flashlight test is a testing for efferent lesions (oculomotor or pupillary muscle lesions). In this case, a much more readily observable response is noted: one eye maintains its normal direct and consensual pupillary reflex to light, whereas the other pupil shows little or no response to either direct or consensual light stimulation.

There are significant drawbacks associated with the traditional swinging-flashlight test. During visual inspection for RAPD, not only must the examiner swing the visible light quickly between the eyes with substantial consistency to achieve relatively valuable and constant data, the examiner must also rely on his or her subjective opinion as to the starting pupil size and speed of the response to light. Needless to say, the traditional test method involves a considerable degree of subjectivity on the part of the examiner because of the inability to measure pupillary response parameters with precision. Furthermore, the lag time between each eye examination may be problematic since consensual pupillary reflex kinetics is preferably measured at the same time for both eyes.

Disadvantages associated with conventional pupilometers make their use unsuitable for RAPD assessment. Besides the aforementioned challenges, pupilometers lack the ability to measure the response in one eye "relative" to the other. Pupilometers with a binocular-type housing design fair no better. For example, one pupilometer, disclosed in U.S. Pat. No. 6,022,109 to Dal Santo, teaches that binocular pupillary response may be measured by simply flipping the disclosed instrument 180 degree after testing of the first eye is completed. Pupillary response data collected in such manner are of little or no value to a truly accurate diagnosis since they are not measured at the same time and under the same conditions. More importantly, pupilometers lack the means for gathering and assessing other ophthalmologic biomarkers. Conventional pupilometers measure, for example, the diameter of a pupil before and after the pupil is exposed to a light stimulus pulse and the rates at which the pupil may constrict and later dilate in response to the initiation and termination of the light stimulation.

Similarly, various devices and techniques exist for detecting and assessing retinal blood vessel coloration, and are generally referred to as retinal oximetry systems or optical oximeters.

The retina provides the opportunity for non-invasive observation of human microcirculation in vivo. Retinal vasculature can be an indicator for monitoring a range of conditions, including exposure to chemical threat agents, which include various biological toxins and chemical agents such as cyanide and carbon monoxide. In general, exposure to chemical threat agents can drastically affect retinal blood vessel coloration. Specifically, a decrease in the brightness of the retinal arteries can indicate possible carbon monoxide exposure. A significant decrease in the brightness of the retinal arteries can lead to a definitive diagnosis of carbon monoxide exposure. In contrast, an increase in the brightness of the retinal veins can indicate possible cyanide exposure. A significant increase in the brightness of the retinal veins can lead to a definitive diagnosis of cyanide exposure. Numerous congenital, vascular, autoimmune, and connective tissue disorders can initially present with an ocular manifestation. For example, a variety of retinal vascular changes can be seen in hypertensive patients; these depend in part on the severity and duration of the hypertension. Common hypertensive retinal changes are characterized by flame-shaped hemorrhages in the superficial layers of the retina and "cotton-wool" patches caused by occlusion of the pre-capillary arterioles with ischemic infarction of the superficial retina. Chronic hypertension can produce arteriolar sclerotic vacuolar changes, such as copper or silver wiring (light reflection colors) of the arterioles or swelling of the blood vessels near the optic disc. Ocular blood vessels include, but are not limited to: arteries, veins, venules, capillaries, and arterioles.

Retinal imagery may also provide valuable information about neurological health by imaging nerves, including the optic nerve within the eyes.

Significant drawbacks exist with conventional optical oximeters that make measuring retinal blood vessel coloration in emergency situations impractical and inadequate. For example, exposure to organophosphate nerve agents and/or botulinum toxin is not evidenced by the retinal blood vessel coloration test. Moreover, conventional optical oximeters are particularly inaccurate when used to identify early blood loss in trauma victims.

There has been a long sought but unfulfilled need for apparatus, methods and systems that automatically and simultaneously measure and assess ophthalmologic biomarkers in one or both eyes to address the concerns described supra.

SUMMARY OF THE INVENTION

Embodiments of the present invention provide for new and improved apparatus, systems and methods that are simple in operation and solve the aforementioned problems, are relatively compact in size, and can simultaneously detect and assess pupillary responsiveness, or lack thereof, and image retinas in one or both eyes.

Embodiments may include a binocular pupillary response scanning apparatus including one or more visible light sources operable to illuminate a first eye and a second eye simultaneously or separately, one or more infrared light sources for continuously illuminating the first eye and the second eye; one or more imaging devices for detecting reflected infrared light from the first eye and the second eye; a converter for converting the reflected infrared light into electrical image signals; and a signal transmitter for transmitting the electrical image signals.

One or more processors may process the electrical image signals. One or more memories may store the electrical image signals. One or more interfaces may transmit the electric image signals to one or more processors for analysis. A display may be provided. A light-blocking enclosure may be provided that has an open end for receiving the first eye and the second eye. A light-blocking divider may be positioned within the light-blocking enclosure for isolating the first eye from the second eye. One or more imaging devices may be charge-coupled device cameras. One or more visible light sources may emit visible light of variable intensities. The one or more infrared light sources may emit light between approximately 700 to approximately 1,000 nm, or between approximately 780 to approximately 860 nm. The binocular pupillary response scanning apparatus may also include retinal scanning apparatus having one or more light sources corresponding to the first eye; one or more light sources corresponding to a second eye; one or more imaging devices for capturing a retinal image of the first eye during illumination of the first eye with the one or more light sources; and one or more imaging devices for simultaneously capturing a retinal image of the second eye during illumination of the second eye with the one or more light sources. As well recognized in the art, the number of electronic components can be reduced using mirrors or beam splitters.

Embodiments may include a method for binocular diagnosis with the steps of providing a binocular scanning apparatus having one or more visible light sources; one or more infrared light sources; and one or more imaging devices; illuminating a first eye and a second eye with infrared light from the one or more infrared light sources; capturing at least one image with the one or more imaging devices; illuminating the first eye with visible light from the one or more visible light sources for a predetermined duration; ceasing illuminating the first eye with visible light for a predetermined duration; capturing at least one image with the one or more imaging devices; illuminating the second eye with visible light from the one or more visible light sources for a predetermined duration; ceasing illuminating the second eye with visible light; and capturing at least one image with the one or more imaging devices.

Pupillary response of the first eye may be compared to pupillary response of the second eye in the captured images. A diagnosis may be formulated based on the results of the comparing step. The steps of illuminating and capturing may be repeated for a predetermined number of cycles. The intensity or wavelength of the visible light may be varied between cycles. A dark field condition may be established around the first eye and the second eye during the illuminating and capturing steps. The captured images may be processed to determine pupillary response measurements. The pupillary response measurements may be selected from the group consisting of pupil reaction/redilation latency, pupil reaction duration, pupil reaction rate, maximal pupil area change, percentage of maximal pupil area change, rebound percentage during redilation, changes in symmetry or asymmetry of the pupil, and combinations thereof. The captured images may be compared to average size and response data from captured images for a population to which the subject belongs. The response measurements may also be charted over time to observe any changes in the pressure on the nerves or brain or continuing damage.

Embodiments may also include a retinal scanning apparatus having one or more light sources corresponding to a first eye; one or more light sources corresponding to a second eye; a light-blocking enclosure for dark-adapting the first eye and the second eye; a light-blocking divider positioned within the light-blocking enclosure for isolating the first eye from the second eye; one or more imaging devices for capturing a retinal image of the first eye during illumination of the first eye with the one or more light sources; and one or more imaging devices for simultaneously capturing a retinal image of the second eye during illumination of the second eye with the one or more light sources. As well recognized in the art, the number of electronic components can be reduced using mirrors or beam splitters.

The one or more light sources may be infrared light sources. The one or more imaging devices may be charge-coupled device cameras. The retinal scanning apparatus may also include a binocular pupillary response scanning apparatus having: one or more visible light sources operable to illuminate the first eye and the second eye simultaneously or separately; one or more infrared light sources for continuously illuminating the first eye and the second eye; and one or more imaging devices for detecting reflected infrared light from the first eye and the second eye. Naturally, said continuous illumination could also be accomplished by rapid pulsing of the illumination.

Embodiments may include a method of scanning a retina including providing a retinal scanning apparatus having one or more infrared light sources for illuminating a first eye; one or more infrared light sources corresponding to a second eye; a light-blocking enclosure for dark-adapting the first eye and the second eye; a light-blocking divider positioned within the light-blocking enclosure for isolating the first eye from the second eye; one or more imaging devices for capturing a retinal image of the first eye during illumination of the first eye with the one or more infrared light sources; and one or more imaging devices for simultaneously capturing a retinal image of the second eye during illumination of the second eye with the one or more infrared light sources; illuminating the first eye with continuous infrared light from the one or more infrared light sources for illuminating the first eye while simultaneously illuminating the second eye with continuous infrared light from the one or more infrared light sources for illuminating the second eye; capturing at least one image of the first eye with the one or more imaging devices for capturing a retinal image of the first eye; capturing at least one image of the first eye with the one or more imaging devices for capturing a retinal image of the first eye; and analyzing the captured images for diagnosing a condition of the first eye and the second eye.

Analysis of the captured images may include tracking blood vessels in the retina; determining retinal blood vessel type; digitizing retinal blood vessel and retina images; normalizing the background and color of the retinal blood vessel and retina images; and establishing an individual-specific retinal standard. The captured images may be stored in a database, wherein the database may include normalized values for retinal standards, wherein the normalized values for retinal standards are a subject's average measurements selected from the group consisting of retina blood vessel coloration, retinal vascular caliber, surface area of the retina covered by blood vessels, and combinations thereof.

The above and other objects, features, and advantages of the present invention will be apparent from the following drawings in conjunction with the accompanying detailed description and claims.

DETAILED DESCRIPTION OF THE PREFERRED EMBODIMENTS

Figure 1:
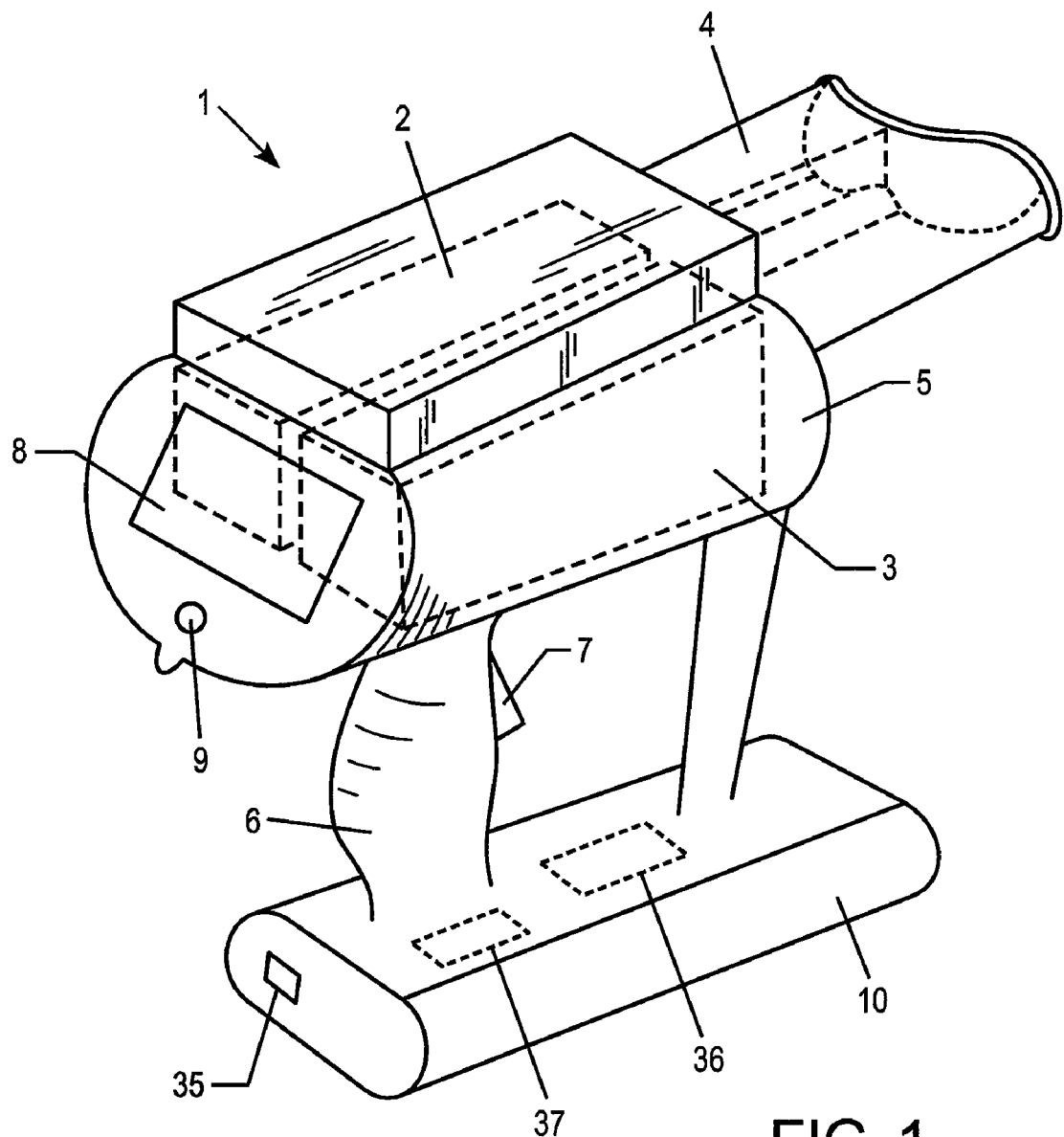
FIG. 1 is a perspective view showing general internal components of an optical scanning apparatus suitable for detecting and assessing pupillary responsiveness and/or taking retinal images.
Figure 2:
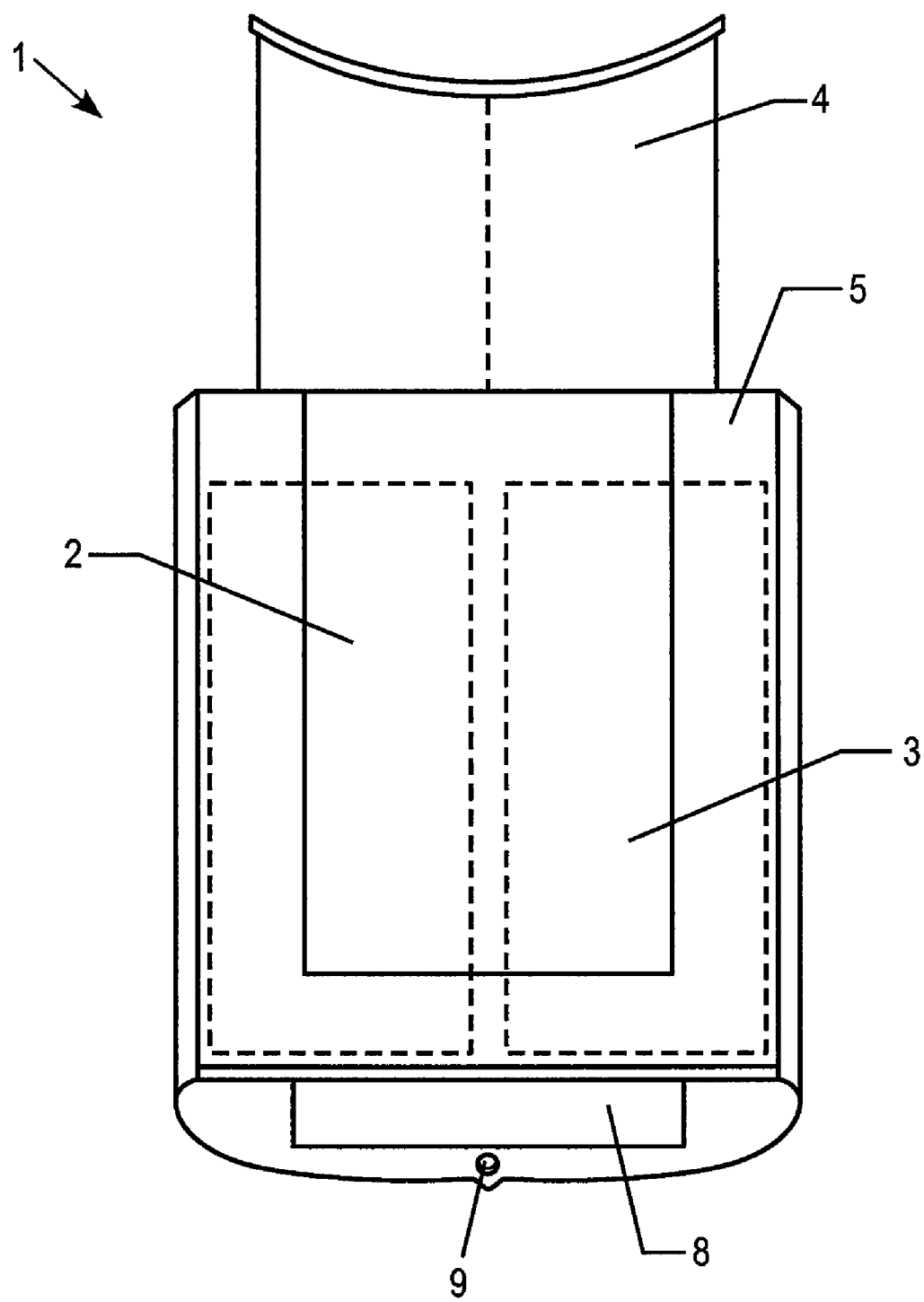
FIG. 2 is a top view showing general internal components of the embodiment shown in FIG. 1.

FIGS. 1 and 2 illustrate an exemplary optical scanning apparatus 1 suitable for detecting and assessing various ophthalmologic biomarkers such as, for example, pupillary responsiveness and retinal imagery. The optical scanning apparatus may take images of the retina and/or the pupil. More specifically, FIGS. 1 and 2 show an apparatus 1 having one or more, but preferably two or more scanning modules 2, 3. The modules 2, 3 may be retinal scanning modules and/or a pupillary response scanning modules. As shown in FIGS. 1 and 2, apparatus 1 may include a subject-end orbital enclosure 4, which may be divided into two chambers, one for each eye, a housing or platform 5 for mounting the scanning modules 2, 3, a handle 6 with an external trigger-like switch or other activator 7 for initiating a scanning process, a liquid crystal or other display screen 8 for displaying resultant images and data, a control button, keypad, or other input mechanism 9, and a portable power source 10.

Figure 3:
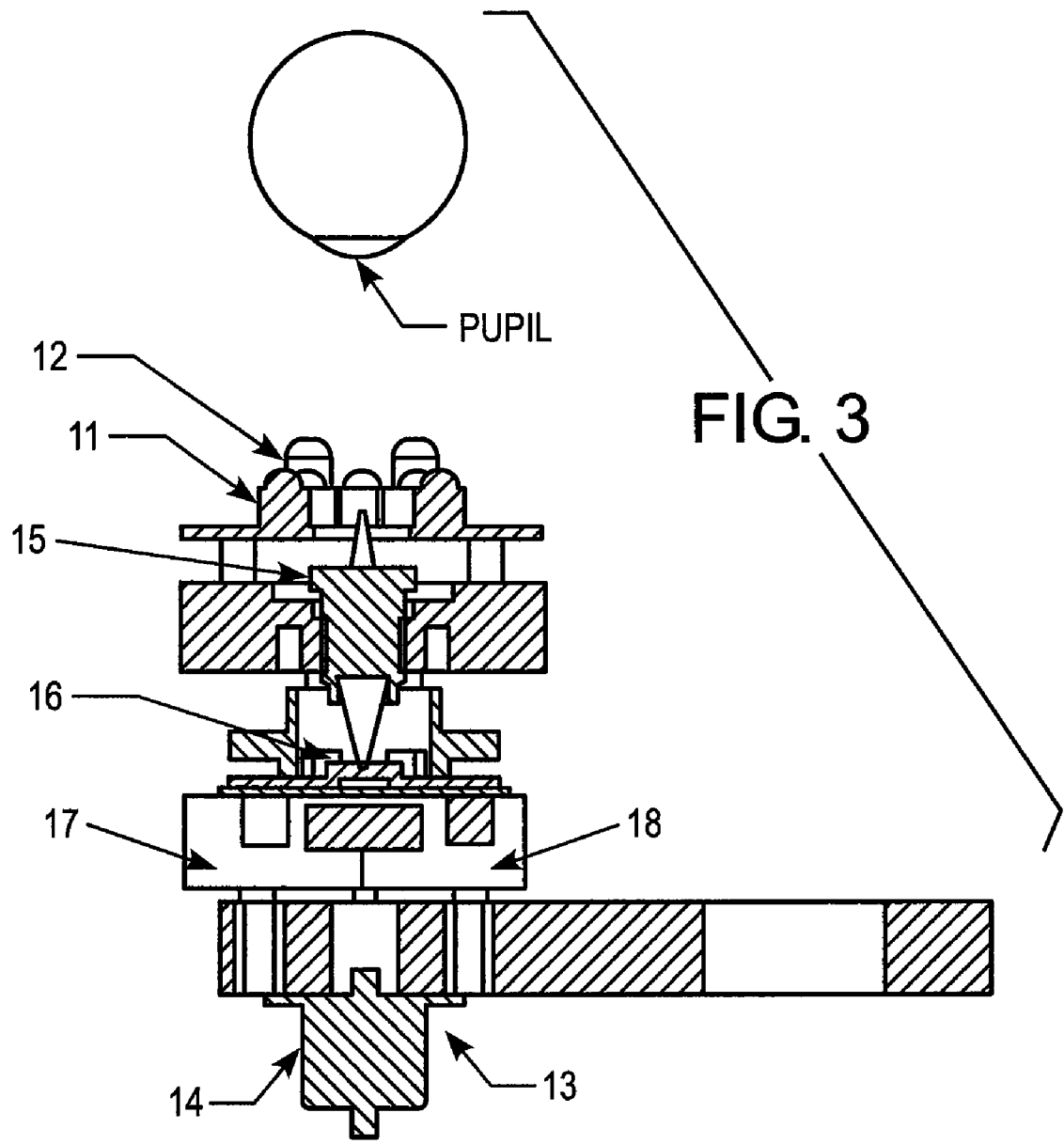
FIG. 3 is a schematic detail of a pupillary scanning module.
Figure 4:
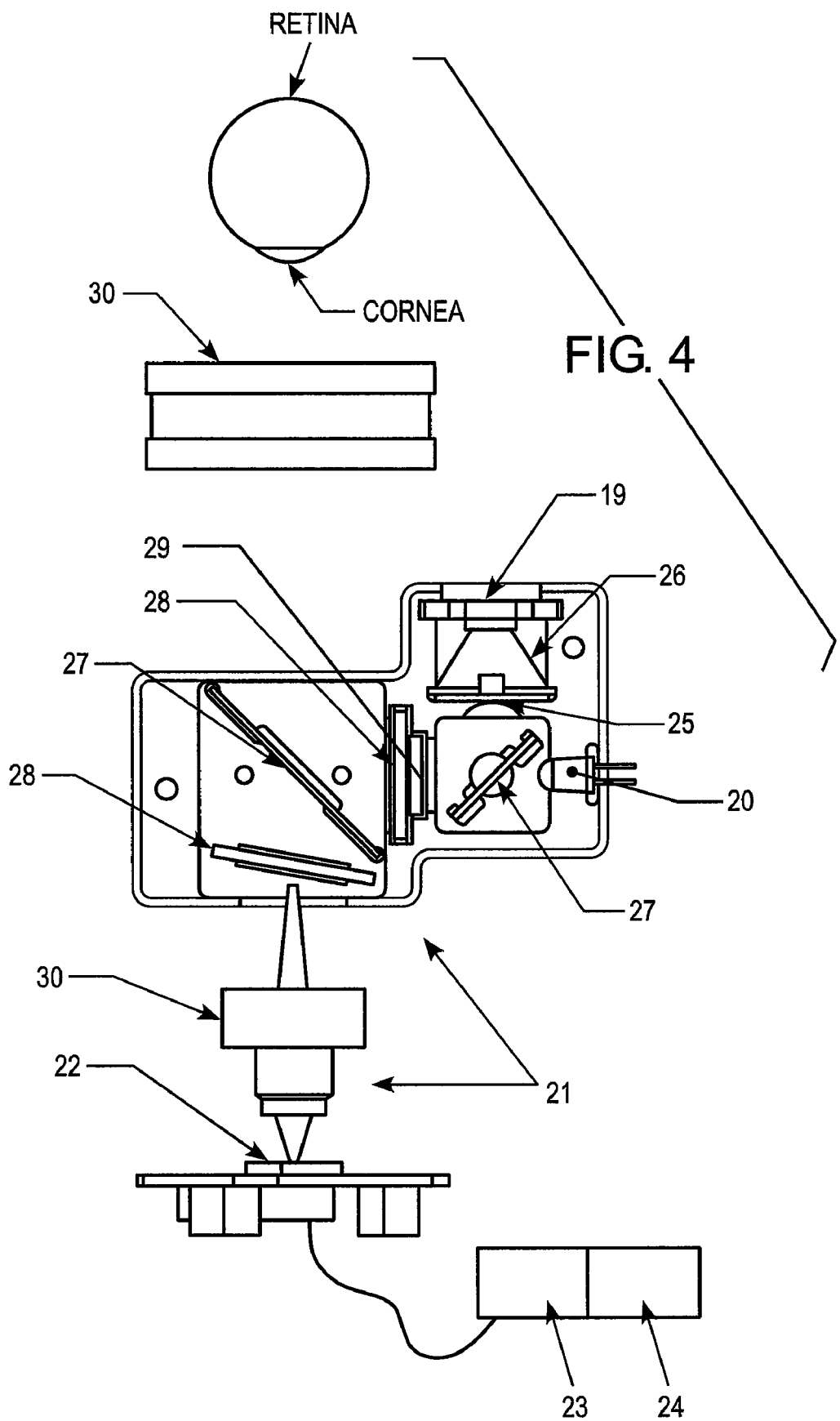
FIG. 4 is a schematic detail of a retinal scanning module.

FIGS. 3 and 4 show an interchangeable pupillary response scanning module and a retinal scanning module, respectively, for measuring various ophthalmologic biomarkers. The pupillary scanning module and the retinal scanning module are preferably modular and interchangeable.

Pupillary Responsiveness

Pupillary responsiveness may be one of the ophthalmologic biomarkers evaluated when examining a subject's eyes. Preferably, each pupil is evaluated to assess whether there has been a significant increase (mydriasis or dilation) or decrease (miosis or constriction) in the diameter of the pupil.

As shown in FIG. 3, the pupillary response scanning module may include a visible light array 11, such as a LED array or other visible light-emitting array. The visible light array 11 may produce visible light of various intensities and/or wavelengths. The pupillary response scanning module may also include an infrared light array 12, such as an LED array or other infrared light-emitting array, capable of emitting infrared light to measure pupillary response.

The pupillary response scanning module may also include a projector 13 that may have an actuator 14 and one or more focusing lenses 15 for projecting infrared light reflected from a subject's pupil. An imaging device 16, such as, for example, a charge-coupled device imaging camera, may be provided for detecting the infrared light reflected from the subject's pupil and capturing image data. A converter 17 may convert detected light and image data into electrical signals, which may then be transmitted via a transmitter 18 to an onboard data processor and memory and/or an external data processor and memory. One or more interfaces 35 may allow transmission of the electrical signals to an external source. The one or more interfaces 35 may be universal serial buses, infrared connections, serial port connections, or other similar devices. One or more memory devices 36 may be included in the apparatus 1. The one or more memory devices 36 may store the electrical signals or the processed information from one or more processors 37. The electrical signals and/or the processed information may be output to the display 8 or to an external source through the one or more interfaces 35.

The pupillary response scanning module may include one or more visible light arrays 11, such as white LEDs, and one or more infrared light arrays 12, such as infrared producing LEDs. The light arrays 11, 12 may be arranged such that both infrared and visible light are directed towards one or more of the subject's eye(s). Preferably, the light arrays 11, 12 are directed towards both of the subject's eyes. Alternatively, there may be light arrays dedicated to each eye where the light arrays provide substantially similar stimulus to each eye during operation of the light arrays.

The light arrays 11, 12 may be operatively connected to the projector 13, imaging device 16, converter 17, and transmitter 18. The light arrays 11, 12 may be operatively associated with one or more focusing lenses 15 such that flashing the visible light array 11 results in light stimuli directed toward the subject's eye to which the subject's pupil responds. The one or more focusing lenses 15 may utilize feedback from the imaging device 16 to automatically bring the pupil into focus using a linear actuator 14.

In accordance with certain embodiments of the present invention, the pupillary response scanning module 3 may detect and measure both absolute as well as relative pupillary size and response data. More specifically, apparatus 1 may determine the relative pupil size and an individual's pupillary response to light stimuli by detecting and measuring the reflected infrared light exiting the individual's pupil, and comparing this relative data with individual-specific baseline data of the pupil being tested to generate actual pupillary size and response data. Alternatively, pupil size and response data may be compared to average size and response data for a population to which the subject belongs.

Figure 5:
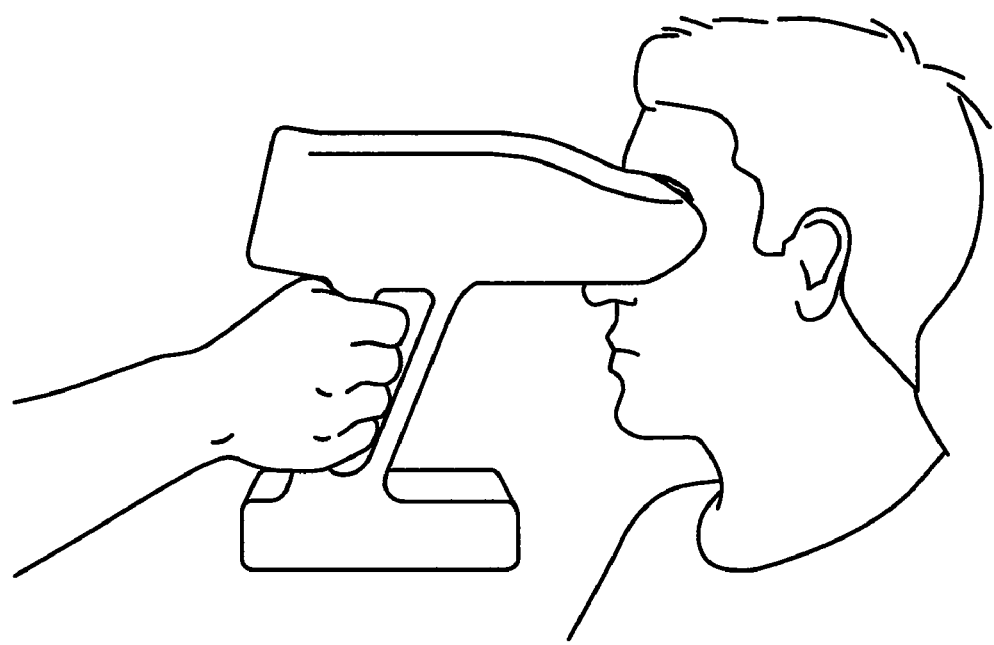
FIG. 5 is a side view of an optical scanning apparatus in use with a subject.

FIG. 5 illustrates a subject being tested on apparatus 1 with the subject-end binocular orbital enclosure 4 pressed against the subject's eye orbitals to diminish and/or prevent light emitted from sources other than the apparatus itself from entering the intended subject's eyes. Preferably, both eyes should be dark-adapted by being in darkness or semidarkness for some time and having undergone dark adaptation to induce maximal pupil dilation.

In accordance with one aspect of the present invention, initial pupillary measurements may be obtained on one or both dark-adapted eyes by continuous illumination with infrared light source 12. Individual-specific baseline data such as baseline static pupil area (SPA; $mm^2$) are measured for each eye. Alternatively, an average pupil size for a population to which the subject belongs can be used as the baseline pupil size for the subject and members of that population.

A testing phase for monocular pupillary responsiveness may involve direct light application. Testing may proceed by stimulating one or both of the subject's eyes with visible light. Preferably, the subject's pupil is evaluated with at least two visible light settings—one with low intensity light (for example, about 1.7 $cd/m^2$), and the second with high intensity light (for example, about 80 $cd/m^2$). Low intensity visible light may be applied to the pupil of the subject's eyes for an arbitrary, predetermined duration ($t_1$). An arbitrary, predetermined duration delay period ($t_2$) may immediately follow $t_1$. During $t_2$, pupillary responsiveness on the stimulated eye may be continuously monitored and measured by projecting an infrared light on the stimulated eye. Infrared wavelengths at or above 700 nm do not stimulate the retina and therefore do not affect the pupillary light reflex. The infrared reflectivity of the iris is much greater than that of the pupil. As a consequence, the amount of reflected infrared light increases when the stimulated pupil constricts. Subtle changes in reflectivity of the subject's eyes may be captured by the imaging device 16, which may convert and transmit the reflected infrared light and subsequent image data into electrical signals by using a converter 17 and a transmitter 18. Electrical signals may then be stored and processed by an onboard processor and memory or an external processor and memory. Any suitable general purpose or special purpose processor and memory can be used to store and process pupillary response images and data consistent with the procedure as set forth. Infrared light may be continuously applied to the patient's eyes during testing. The imaging device 16 may acquire images at predetermined frequencies or stages of the testing phase, including before, during and after visible light illumination. For example, at least one image may be acquired before an initial visible light illumination, at least one image may be acquired between visible light illuminations and at least one image may be acquired after a final visible light illumination. Images may also be acquired during visible light illumination.

A significant decrease in pupil size (miosis) in low intensity light can indicate organophosphate exposure. Specifically, organophosphate exposure can be evaluated by examining whether a subject's pupils retain their ability to contract and dilate in response to altering light conditions (pupillary light reflex). Pupils retain their pupillary light reflex when exposed to relatively low levels of an organophosphate. The pupillary light reflex is eliminated, however, when subjects are exposed to relatively high levels of an organophosphate. Elimination of pupillary light reflex (or significant reduction in the ability to response) is a strong indication of exposure to relatively high levels of organophosphate. In contrast, those exposed to low levels will retain pupillary light reflex. This aspect of the invention can be especially useful in triaging casualties in military field operations where masses of military personnel can possibly be exposed to chemical warfare agents at the same time.

Figure 6:
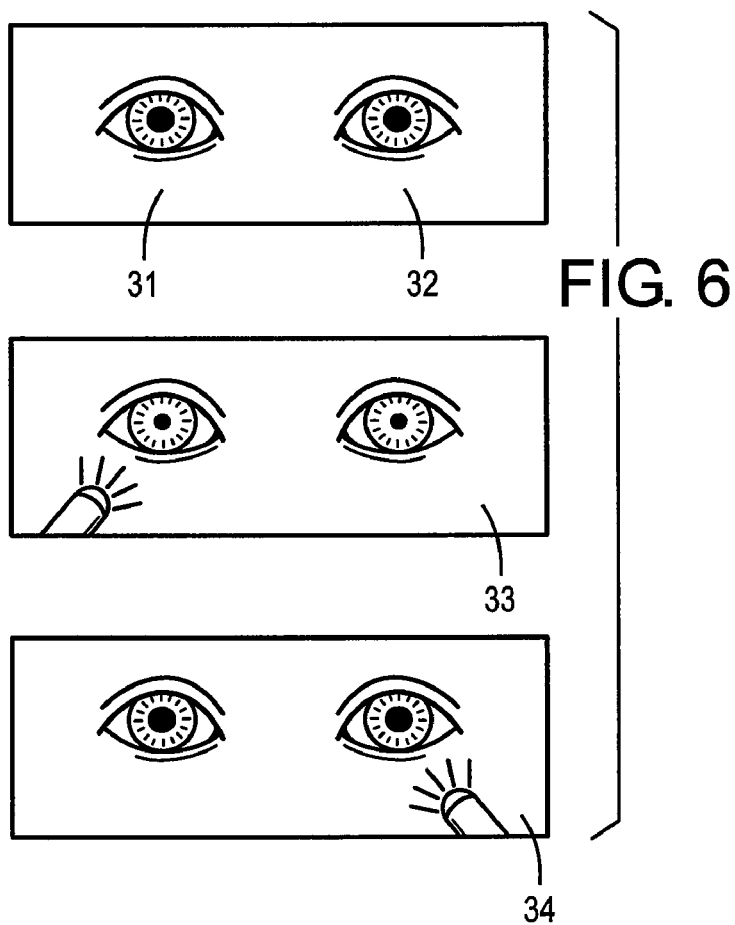
FIG. 6 shows visible light stimuli being applied to a subject's eyes.

Binocular pupillary responsiveness testing may involve consensual light application, generally depicted in FIG. 6. Initial baseline data may be obtained during a dark adaptation period for both eyes 31, 32. Initially, both eyes 31, 32 should have approximately the same dilation. The conditions of the eyes 31, 32 may be measured and compared against each other. A testing phase for pupillary responsiveness of the second eye 32 begins by stimulating the first eye 31 with consensual light application 33. Visible light of a predetermined intensity may be applied to pupil of the first eye 31 for an arbitrary, predetermined light application duration ($t_1$). An arbitrary, predetermined duration delay period ($t_2$) immediately follows $t_1$. During $t_2$, pupillary responsiveness of the non-stimulated eye 32 may be continuously monitored and measured by projecting a non-stimulating infrared light on the second eye 32. Subtle changes in reflectivity of the second eye 32 may be captured by the imaging device 16, which may convert and transmit the reflected infrared light and image data into electrical signals by using the converter 17 and transmitter 18. Electrical signals may then be stored and processed by the onboard processor and memory. To quantify a RAPD, the testing phase may be reinitiated 34 using alternative values for some or all of light intensity, light application duration $t_1$, and light delay duration $t_1$. Values may be manually selected or be selected according to an adaptive algorithm such as a modified binary sequence or staircase procedure. For example, since the light intensity level at which no RAPD is detected is considered the threshold for the defect (and thus a valuable gauge of casualty severity an adaptive algorithm may be incorporated to automatically adjust the parameters to quantify the threshold without the need for user input.

Based upon images and data acquired and analyzed for pupil area of each eye during $t_1$ and $t_2$, the following parameters may be determined and compared for the first eye 31 versus the second eye 32:

1. Pupil reaction latency or pupil redilation latency (PRL; msec)=time between light initiation and pupil constriction/dilation, determined by a predetermined percentage change in pupil size from SPA;

2. Magnitude of maximal pupil area change (MPA; $mm^2$) =difference between SPA and area at point of maximal change (RA), which is the largest area for dilation or the smallest area for constriction;

3. Percent of maximal pupil area change (PPA; %)=MPA divided by SPA

4. Pupil reaction duration (PRD; msec)=time between beginning of pupil reaction and time of maximal change;

5. Pupil reaction rate or pupil contraction/dilation velocity (PRR; $mm^2$/msec)=MPA divided by PRD;

6. Rebound percentage during redilation (RPR; in %)=the difference between the smallest area after constriction and the area after redilation divided by SPA.

7. If multiple reactions occur (both pupillary constriction and dilation) prior to re-initiating the testing phase, the first to occur will have the above five values determined (PRL, MPA, PPA, PRD and PRR) and the extent of the second reaction will be determined by measuring the area of the pupil at the point of maximal change (RA) and MPA, PPA, PRD and PRR with respect to RA (instead of SPA; i.e., substitute RA for SPA).

Retinal Imagery

Retinal imagery is another ophthalmologic biomarker that may be evaluated when examining a subject's eyes. Because retinal imagery has a direct correlation to retinal blood vessel oxygen saturation level, retinal imagery is preferably examined to assess whether there has been a significant change, e.g., increase brightness or darkness, of the blood in the retinal blood vessels. Retinal blood vessels include, but not limited to: arteries, veins, venules, capillaries, and arterioles. Retinal imagery may also be used to view and analyze other aspects of the retina, such as nerve conditions.

As shown in FIG. 4, the retinal scanning module may include an infrared light array 20, such as an LED array or other infrared light arrays. The infrared light array 20 may emit infrared light for tracking, focusing, and aligning the retina with an imaging device 22, such as a charge-coupled device imaging camera. The retinal scanning module may include a projector 21 for projecting infrared light to and back from the retina. An imaging device 22 may be provided for detecting infrared light reflected from the retina and capturing image data. A converter 23 may convert the captured imaged data and detected light into electrical signals, and a transmitter 24 may transmit the electrical signals to an onboard processor and memory or an external processor and memory.

The projector 21 may include one or more of the following: an illumination aperture 25 for controlling the infrared light intensity, one or more columnating lenses 26 for controlling the geometry of the infrared light, additional lenses 19, one or more optical beam splitters 27 for splitting light into beams of differing polarization, one or more polarizers 28 for converting unpolarized light into a polarized state, one or more optical filters 29 for blocking light with a particular range of wavelengths, and an auto-linear actuator with one or more focusing lenses 30 for focusing the infrared light to the retina and back to the imaging device 22.

To determine whether there has been a significant change in retinal blood vessel coloration, a baseline, or "normal," color preferably is first established for certain retinal blood vessels, e.g., retinal veins and arteries. In accordance with one aspect of the present invention, initial retinal blood vessel coloration measurements may be obtained and quantitatively analyzed on one or both dark-adapted eyes by illumination with the light array 20. The infrared light array 20 may be operatively connected to the imaging 22, converter 23, and transmitter 24, and operatively associated with one or more focusing lenses 30 controlled by a linear actuator in such a way that the infrared light is directed towards the subject's retina and back to the imaging device 22.

FIG. 4 illustrates one portion of an exemplary embodiment having an infrared light array 20 that can emit variable infrared light, preferably with a wavelength between approximately 700 nm and approximately 1,000 nm, and more preferably between approximately 780 and approximately 860 nm. Infrared light produced by the infrared light array 20 may be filtered by one or more optical filters 29 and projected onto the retina and back to the imaging device 22 with one or more lenses 30. The reflected infrared light may be captured by the imaging device 22, which converts the reflected infrared light into electrical signals by using the converter 23. Electrical signals may then be transmitted by the transmitter 24 to the onboard processor and memory or an external processor and memory. A number of different digital signal processing methods may be used for optimizing the discrimination capabilities of the system while accounting for the expected variability between individuals. Exemplary embodiments may use all available wavelengths of light to analyze retinal images with greater sensitivity. Any suitable general purpose or special purpose processor and memory can be used to store and process retinal images and data consistent with the procedure as set forth.

The focusing lens or lenses 30 may utilize feedback from the imaging device 22 to automatically bring the retina into focus. Exemplary embodiments may preferably use a 3-charge-coupled device imaging camera instead of a charge-coupled device imaging device to increase resolution. Pattern recognition software may be utilized to locate the optic disk area by finding, for example, the circular pattern of the optic nerve area. After using the pattern recognition information to more precisely locate the optic nerve area in the center of the viewing field, the image may then be magnified using focus lenses 30 such that the optic disk area virtually fills the active area of the imaging device 22.

In preferred embodiments, pupillary response and retinal scanning modules may be generally similar in shape and size, and may be interchangeable. The modules may be encased in or, alternatively, mounted on a portable enclosure or platform with one or more handles and a portable power source.

Exemplary embodiments may have one or more of the following advantages: binocular application of variable intensity light to each eye for measuring ophthalmologic biomarkers in both eyes at the same time; continuous infrared imaging capability that allows imaging at all times; lightweight, compact, and ergonomically designed features for one or two hand operation; automated testing such that once testing sequence is initialized, all light applications, image acquisitions, and data analyses are performed and sequenced by the device (via algorithms) without user intervention; simultaneous image acquisition by streaming images and analysis of pupillary reflexes/reactions (or lack thereof) in one or both eyes captured and compared before, during, and after all light applications to either eye; autonomous features that include on-board processors and a display means; visible environment control capability that covers both eyes and prevents light emitted from sources other than the device itself from entering the subject's eyes; timing control capability which allows the apparatus to perform tests with precise timing of light application (and removed; and/or measuring devices that may allow the apparatus to detect and measure both absolute and relative pupillary size and response data by noting any differences in pupillary reactions (delay, extent, and speed) as well as the extent/amount of these differences.

Although the foregoing description is directed to the preferred embodiments of the invention, it is noted that other variations and modifications will be apparent to those skilled in the art, and may be made without departing from the spirit of the invention. Moreover, features described in connection with one embodiment of the invention may be used in conjunction with other embodiments, even if not explicitly stated above.

The invention claimed is:

1. A binocular pupillary response scanning apparatus comprising:
   one or more visible light sources operable to illuminate a first eye and a second eye simultaneously or separately during testing;
   one or more infrared light sources for continuously illuminating the first eye and the second eye during testing;
   one or more imaging devices for detecting reflected infrared light from the first eye and the second eye;
   a converter for converting the reflected infrared light into electrical image signals;
   a signal transmitter for transmitting the electrical image signals; and
   a processor for comparing the electrical image signals to a baseline for determining pupil area change.

2. The apparatus of claim 1, wherein the processor processes the electrical image signals.

3. The apparatus of claim 1, further comprising one or more memories for storing the electrical image signals.

4. The apparatus of claim 1, further comprising one or more interfaces for transmitting the electric image signals to the processor.

5. The apparatus of claim 1, further comprising a display.

6. The apparatus of claim 1, further comprising a light-blocking enclosure with an open end for receiving the first eye and the second eye.

7. The apparatus of claim 6, further comprising a light-blocking divider positioned within the light-blocking enclosure for isolating the first eye from the second eye.

8. The apparatus of claim 1, wherein the one or more imaging devices are charge-coupled device cameras.

9. The apparatus of claim 1, wherein the one or more visible light sources emit visible light of variable intensities.

10. The apparatus of claim 1, wherein the one or more infrared light sources emit light between approximately 700 to approximately 1,000 nm.

11. The apparatus of claim 10, wherein the one or more infrared light sources emit light between approximately 780 to approximately 860 nm.

12. The apparatus of claim 1, further comprising a retinal scanning apparatus comprising one or more light sources corresponding to the first eye; one or more light sources corresponding to a second eye; one or more imaging devices for capturing a retinal image of the first eye during illumination of the first eye with the one or more light sources; and one or more imaging devices for simultaneously capturing a retinal image of the second eye during illumination of the second eye with the one or more light sources.

13. A method for binocular diagnosis comprising:
   providing a binocular scanning apparatus comprising:
      one or more visible light sources;
      one or more infrared light sources; and
      one or more imaging devices;
   continuously illuminating a first eye and a second eye with infrared light from the one or more infrared light sources during testing;
   capturing at least one baseline image of the first eye or the second eye with the one or more imaging devices;
   illuminating the first eye or the second eye with visible light from the one or more visible light sources for a predetermined duration;
   capturing at least one test image of the first eye or the second eve with the one or more imaging devices during testing;
   transmitting the at least one test image to a processor;
   comparing the at least one test image with at least one baseline; and
   determining pupil area change.

14. The method of claim 13, further comprising comparing pupillary response of the first eye to pupillary response of the second eye in the captured images.

15. The method of claim 14, further comprising formulating a diagnosis based on the comparing step.

16. The method of claim 13, further comprising repeating the illuminating and capturing steps for a predetermined number of cycles.

17. The method of claim 16, further comprising varying the intensity of the visible light between cycles.

18. The method of claim 13, further comprising establishing a dark field condition around the first eye and the second eye during the illuminating and capturing steps.

19. The method of claim 13, further comprising processing the captured images to determine pupillary response measurements.

20. The method of claim 19, wherein the pupillary response measurements are selected from the group consisting of pupil reaction/redilation latency, pupil reaction duration, pupil reaction rate, maximal pupil area change, percentage of maximal pupil area change, rebound percentage during redilation, and combinations thereof.

21. The method of claim 13, wherein the baseline is average size and response data from captured images for a population to which the subject belongs.

22. A retinal scanning apparatus comprising:
   one or more light sources corresponding to a first eye;
   one or more light sources corresponding to a second eye;
   a light-blocking enclosure for dark-adapting the first eye and the second eye;
   a light-blocking divider positioned within the light-blocking enclosure for isolating
      the first eye from the second eye;
   one or more imaging devices for capturing a retinal image of the first eye during illumination of the first eye with the one or more light sources;

one or more imaging devices for simultaneously capturing a retinal image of the second eye during illumination of the second eye with the one or more light sources; and a processor for locating an optical disk in the retinal image of the first eye and the retinal image of the second eye and determining retinal blood vessel oxygen saturation levels or nerve conditions.

23. The apparatus of claim 22, wherein the one or more light sources are infrared light sources.

24. The apparatus of claim 22, wherein the one or more imaging devices are charge-coupled device cameras.

25. The apparatus of claim 22, further comprising a binocular pupillary response scanning apparatus comprising: one or more visible light sources operable to illuminate the first eye and the second eye simultaneously or separately; one or more infrared light sources for continuously illuminating the first eye and the second eye; and one or more imaging devices for detecting reflected infrared light from the first eye and the second eye.

26. A method of scanning a retina comprising:
providing a retinal scanning apparatus comprising:
one or more infrared light sources for illuminating a first eye;
one or more infrared light sources corresponding to a second eye;
a light-blocking enclosure for dark-adapting the first eye and the second eye;
a light-blocking divider positioned within the light-blocking enclosure for isolating the first eye from the second eye;
one or more imaging devices for capturing a retinal image of the first eye during illumination of the first eye with the one or more infrared light sources; and
one or more imaging devices for simultaneously capturing a retinal image of the second eye during illumination of the second eye with the one or more infrared light sources;

illuminating the first eye with continuous infrared light from the one or more infrared light sources for illuminating the first eye while simultaneously illuminating the second eye with continuous infrared light from the one or more infrared light sources for illuminating the second eye;

capturing at least one image of the first eye with the one or more imaging devices for capturing a retinal image of the first eye;

simultaneously capturing at least one image of the second eye with the one or more imaging devices for capturing a retinal image of the second eye;

locating an optical disk in the retinal image of the first eye and the retinal image of the second eye and determining retinal blood vessel oxygen saturation levels or nerve conditions; and analyzing the captured images for diagnosing a condition of the first eye and the second eye.

27. The method of claim 26, wherein analyzing the captures images further comprises:
tracking blood vessels in the retina;
determining retinal blood vessel type;
digitizing retinal blood vessel and retina images;
normalizing the background and color of the retinal blood vessel and retina images; and
establishing an individual-specific retinal standard.

28. The method of claim 26, wherein the captured images are stored in a database, wherein the database further comprises normalized values for retinal standards, wherein the normalized values for retinal standards are a subject's average measurements selected from the group consisting of retina blood vessel coloration, retinal vascular caliber, surface area of the retina covered by blood vessels, and combinations thereof.

* * * * *